United States Patent
Schjødt et al.

(10) Patent No.: US 12,215,432 B2
(45) Date of Patent: Feb. 4, 2025

(54) METHOD FOR GENERATING SYNTHESIS GAS FOR USE IN HYDROFORMYLATION REACTIONS

(71) Applicant: HALDOR TOPSØE A/S, Kgs. Lyngby (DK)

(72) Inventors: Niels Christian Schjødt, Hvalsø (DK);
Rainer Küngas, Copenhagen (DK);
Berit Hinnemann, Stenløse (DK);
Bengt Peter Gustav Blennow, Humlebæk (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 1071 days.

(21) Appl. No.: 17/046,049

(22) PCT Filed: Apr. 11, 2019

(86) PCT No.: PCT/EP2019/059201
§ 371 (c)(1),
(2) Date: Oct. 8, 2020

(87) PCT Pub. No.: WO2019/197514
PCT Pub. Date: Oct. 17, 2019

(65) Prior Publication Data
US 2021/0130965 A1 May 6, 2021

(30) Foreign Application Priority Data
Apr. 13, 2018 (DK) .......................... PA 2018 00156

(51) Int. Cl.
| | |
|---|---|
| *C25B 1/23* | (2021.01) |
| *C01B 3/06* | (2006.01) |
| *C01B 32/40* | (2017.01) |
| *C10K 1/04* | (2006.01) |
| *C10K 3/02* | (2006.01) |
| *C25B 1/042* | (2021.01) |
| *C25B 9/19* | (2021.01) |
| *C25B 9/70* | (2021.01) |
| *C25B 13/05* | (2021.01) |
| *C25B 13/07* | (2021.01) |
| *C25B 15/021* | (2021.01) |
| *C25B 15/08* | (2006.01) |

(52) U.S. Cl.
CPC .................. *C25B 1/23* (2021.01); *C01B 3/06* (2013.01); *C01B 32/40* (2017.08); *C10K 1/04* (2013.01); *C10K 3/026* (2013.01); *C25B 1/042* (2021.01); *C25B 9/19* (2021.01); *C25B 9/70* (2021.01); *C25B 13/05* (2021.01); *C25B 13/07* (2021.01); *C25B 15/021* (2021.01); *C25B 15/08* (2013.01); *C25B 15/081* (2021.01); *C25B 15/083* (2021.01); *C01B 2203/02* (2013.01); *C01B 2203/0495* (2013.01); *C01B 2203/06* (2013.01); *C01B 2203/12* (2013.01)

(58) Field of Classification Search
CPC ....... C25B 1/23; C25B 1/042; C01B 2203/02; C01B 2203/12; Y02E 60/36
See application file for complete search history.

(56) References Cited

U.S. PATENT DOCUMENTS

| | | | |
|---|---|---|---|
| 7,365,234 B2 | 4/2008 | Subramaniam et al. | |
| 7,750,494 B1 | 7/2010 | Behrens et al. | |
| 8,568,581 B2 | 10/2013 | Sivasankar et al. | |
| 2008/0023338 A1 | 1/2008 | Stoots et al. | |
| 2009/0014336 A1 | 1/2009 | Olah et al. | |
| 2011/0206566 A1 | 8/2011 | Stoots et al. | |
| 2011/0253550 A1 | 10/2011 | Hoffmann | |
| 2012/0201717 A1 | 8/2012 | Singh et al. | |
| 2013/0178657 A1 | 7/2013 | Franke et al. | |
| 2014/0194539 A1 | 7/2014 | Hammad et al. | |
| 2014/0288195 A1 | 9/2014 | Castelli et al. | |

(Continued)

FOREIGN PATENT DOCUMENTS

| | | |
|---|---|---|
| JP | 2010-533784 A | 10/2010 |
| JP | 2016-511296 A | 4/2016 |

(Continued)

OTHER PUBLICATIONS

Jin et al, "Homogeneous Catalytic Hydroformylation of 1-Octene in CO2-Expanded Solvent Media," Chemical Engineering Science, 59 (2004) 4887-4893 (Year: 2004).*

Kazempoor et al, Hydrogen and Synthetic Fuel Production using High Temperature Solid Oxide Electrolysis Cells (SOECs). International Journal of Hydrogen Energy, 40 (2015) 3599-3612 (Year: 2015).*

Office Action (National Intellectual Property Office) issued on Sep. 29, 2022, by the Chinese Patent Office in corresponding Chinese Patent Application No. 201980025287.4, and an English Translation of the Office Action. (13 pages).

Kazempoor, P. et al. "Hydrogen and synthetic fuel production using high temperature solid oxide electrolysis cells (SOECs)" Elsevier, International Journal of Hydrogen Energy, vol. 40, 2015, pp. 2599-3612.

Fang, J., et al, "Economic and Environmental Impact Analyses of Catalytic Olefin Hydroformylation in CO2-Expanded Liquid (CXL) Media," Ind. Eng. Chem. Res., 46, pp. 8687-8692 (2007).

(Continued)

*Primary Examiner* — Salil Jain
(74) *Attorney, Agent, or Firm* — Boone IP Law

(57) ABSTRACT

A method for the generation of a gas mixture including carbon monoxide, carbon dioxide and hydrogen for use in hydroformylation plants, including the steps of evaporating water to steam; feeding the steam to a solid oxide electrolysis cell (SOEC) or an SOEC stack at a sufficient temperature for the cell or cell stack to operate while effecting a partial conversion of steam to hydrogen; utilizing the effluent SOEC gas including $H_2$ together with $CO_2$ from an external source as feed for a RWGS reactor in which the RWGS reaction takes place, converting some of the $CO_2$ and $H_2$ to CO and $H_2O$; removing some of or all the remaining steam from the raw product gas stream; using said gas mixture comprising CO, $CO_2$ and $H_2$ for liquid phase hydroformylation utilizing carbon monoxide and hydrogen as reactants, while recycling $CO_2$ to the RWGS reactor.

5 Claims, No Drawings

(56) References Cited

U.S. PATENT DOCUMENTS

| | | |
|---|---|---|
| 2014/0291162 A1 | 10/2014 | Sala et al. |
| 2016/0040311 A1 | 2/2016 | Jakobsson |
| 2016/0053388 A1 | 2/2016 | Reytier et al. |
| 2017/0218404 A1 | 8/2017 | Simpson |
| 2018/0066371 A1 | 3/2018 | Hong et al. |
| 2018/0086985 A1* | 3/2018 | von Olshausen ....... C25B 15/02 |

FOREIGN PATENT DOCUMENTS

| | | |
|---|---|---|
| JP | 2016-522166 A | 7/2016 |
| WO | 2007025280 A2 | 3/2007 |
| WO | 2007109549 A2 | 9/2007 |
| WO | 2008/016728 A2 | 2/2008 |
| WO | 2008124538 A1 | 10/2008 |
| WO | 2013164172 A1 | 11/2013 |
| WO | 2014107561 A1 | 7/2014 |
| WO | 2017014635 A1 | 1/2017 |
| WO | 2017141138 A1 | 8/2017 |
| WO | 2018051334 A1 | 3/2018 |

OTHER PUBLICATIONS

Fujita, S., et al., "Hodroformylation of Cyclohexene with Carbon Dioxide and Hydrogen Using Ruthenium Carbonyl Catalyst: Influence of Pressures of Gaseous Components," International Journal of Molecular Sciences, 8, pp. 749-759 (2007).

Gaudillere, C., et al. "Syngas production at intermediate temperature through H2O and CO2 electrolysis with a Cu-based solid oxide electrolyzer cell," ScienceDirect, International Journal of Hydrogen Energy, 39, pp. 3047-3054 (2014).

Hong, J., et al., "Homogeneous catalytic hydroformylation of 1-octene in CO2-expanded solvent media," Chemical Engineering Science, 59, 4887-4893 (2004).

International Search Report and Written Opinion issued in corresponding International Patent Application No. PCT/EP2019/059201, 9 pages (Jul. 22, 2019).

International Search Report and Written Opinion issued in corresponding International Patent Application No. PCT/EP2019/059204, 10 pages (Jun. 19, 2019).

Jin H., et al, "Homogeneous catalytic hydroformylation of 1-octene in CO2-expanded solvent media," Chemical Engineering Science, 59, pp. 4887-4893 (2004).

Jin H., et al, "Intensification of Catalytic Olefin Hydroformylation in CO2-Expanded Media," AIChE Journal, 52:7, pp. 2575-2581 (2006).

Lizhen, G., et al., "Demonstration of direct conversion of CO2/H2O into syngas in a symmetrical proton-conducting solid oxide electrolyzer," ScienceDirect, International Journal of Hydrogen Energy, 41, pp. 1170-1175 (2016).

Search Report issued in corresponding Danish Patent Application No. PA201800155, 8 pages (Oct. 9, 2018).

Search Report issued in corresponding Danish Patent Application No. PA201800156, 8 pages (Nov. 6, 2018).

Wang, Y., et al., "Syngas production on a symmetrical solid oxide H2O/CO2 co-electrolysis cell with Sr2Fe1.5Mo0.5O6-Sm0.2Ce0.8O1.9 electrodes," Journal of Power Sources, 305, pp. 240-248 (2016).

Zhao, K., et al., "Reverse water gas shift reaction over CuFe/Al$_2$O$_3$ catalyst in solid oxide electrolysis cell," Chemical Engineering Journal, 336, pp. 20-27 (2018).

* cited by examiner

METHOD FOR GENERATING SYNTHESIS GAS FOR USE IN HYDROFORMYLATION REACTIONS

TECHNICAL FIELD

The present invention relates to a method for generating a gas comprising carbon monoxide and hydrogen and its use in hydroformylation reactions.

BACKGROUND

Hydroformylation, also known as "oxo synthesis" or "oxo process", is an industrial process for the production of aldehydes from alkenes. More specifically, the hydroformylation reaction is the addition of carbon monoxide (CO) and hydrogen (Hz) to an alkene. This chemical reaction entails the net addition of a formyl group (CHO) and a hydrogen atom to a carbon-carbon double bond. The reaction yields an aldehyde with a carbon chain one unit longer than that of the parent alkene. If the aldehyde is the desired product, then the syngas should have a composition close to $CO:H_2=1:1$.

In some cases, the alcohol corresponding to the aldehyde is the desired product. When this is the case, more hydrogen is consumed to reduce the intermediate aldehyde to an alcohol, and therefore the syngas should have a composition of approximately $CO:H_2=1:2$.

Sometimes it is desired to purify the intermediate aldehyde before converting it into an alcohol. Accordingly, in such case, a syngas with the composition $CO:H_2=1:1$ must first be used, followed by pure $H_2$.

Thus, the need for low-module syngas (i.e. syngas with a low hydrogen-to-carbon monoxide ratio) is characteristic for the hydroformylation reaction. Such syngas compositions are rather costly to provide since they cannot be obtained directly from steam reforming of natural gas or naphtha. At least, a cold box for condensing CO has to be installed to separate the CO. This is a costly solution, and there will be an excess of hydrogen for which a use purpose has to be found.

Alternatively, gasification plants may provide low-module syngas, but gasification plants need to be very large to be efficient, and they are expensive, both with respect to CAPEX and to OPEX. Furthermore, coal-based gasification plants are increasingly undesired due to the substantial environmental implications and a large $CO_2$ footprint.

Low-module (i.e. CO-rich) syngas for hydroformylation is therefore generally costly. Large hydroformylation plants are often placed in industrial areas and may thus obtain the necessary syngas "over the fence" from a nearby syngas producer. In many cases, however, this is not possible for medium or small size hydroformylation plants. Instead, such smaller plants will need to import the syngas, e.g. in gas cylinders, and this approach is very expensive. Furthermore, transportation and handling of such gas containers is connected with certain elements of risk since syngas (not least low-module syngas) is highly toxic and extremely flammable, and syngas may form explosive mixtures with air. Import of CO or syngas by tube trailers will face similar challenges, both in terms of costs and in terms of safety.

A sustainable source of CO is $CO_2$. By means of the reverse water gas shift (RWGS) reaction, i.e. the reaction $$CO_2+H_2 \leftrightarrow CO+H_2O$$

carbon monoxide can be generated from carbon dioxide. The hydrogen used for the reaction can be generated from steam using a solid oxide electrolysis cell (SOEC) or an SOEC stack. According to the present invention, $H_2$ is generated from steam in an SOEC or an SOEC stack at an elevated temperature, typically close to 700° C. The effluent gas from the SOEC or SOEC stack will contain $H_2$ and $H_2O$ at a temperature close to the operating temperature of the SOEC. This effluent gas may be led directly to a RWGS reactor together with $CO_2$. The RWGS reactor is typically a heated reactor but may also be an adiabatic reactor. In the RWGS reactor, the above RWGS reaction proceeds.

Since the RWGS reaction is equilibrium limited, the effluent gas from the RWGS reactor will contain $H_2$, CO, $H_2O$ and $CO_2$. Water is removed by cooling the effluent gas until the majority of the steam condenses as liquid water. Further drying of the gas may be achieved by using e.g. a drying column. The $CO_2$ can be removed by using e.g. a pressure swing adsorption (PSA) apparatus, but such apparatus is very costly. According to the present invention, $CO_2$ is not removed until after the hydroformylation reaction. This is cost saving and presents an additional advantage.

It has been shown for the hydroformylation reaction that the rate may be increased up to four-fold by conducting the reaction in $CO_2$-expanded liquid (CXL) media (see e.g. H. Jin and B. Subramaniam, *Chemical Engineering Science* 59 (2004) 4887-4893 and H. Jin et al., AIChE Journal 52 (2006) 2575-2581). Pressurizing an organic solvent with $CO_2$ makes it expand and increases the diffusivity and solubility of other (reactant) gases compared to the neat solvent. The use of CXL media is a general way of intensifying liquid phase catalytic reactions, such as carbonylation reactions. However, a source of $CO_2$ as well as a source of CO and a source of $H_2$ is needed, which is not always feasible. The present invention is aimed at solving these problems.

SUMMARY

So the present invention relates to a novel method for the generation of a gas mixture comprising carbon monoxide, carbon dioxide and hydrogen for use in hydroformylation plants. Through the method of the invention, the above problems combined are turned into an advantage. By combining high-temperature electrolysis of steam (forming hydrogen) with the RWGS reaction (forming carbon monoxide), a low-module syngas may be obtained. Thus, carbon dioxide will serve as the sole source of carbon monoxide, and therefore, any storage, transportation and handling of carbon monoxide will be omitted. Furthermore, the presence of carbon dioxide in the reaction medium will provide the conditions for CXL, which will increase the reaction rate of the hydroformylation reaction.

It is the intention of the present invention to provide a syngas generating apparatus based on solid oxide electrolysis cells (SOECs) in combination with a reverse water gas shift (RWGS) reactor, which can generate syngas for hydroformylation plants. The raw materials for generating the syngas will be $H_2O$ and $CO_2$.

Regarding prior art, U.S. Pat. No. 8,568,581 discloses a hydroformylation process using a traditional electrochemical cell, not a solid oxide electrolysis cell (SOEC) or an SOEC stack, for preparation of the synthesis gas to be used in the process. Water is introduced in a first (anode) compartment of the cell, and $CO_2$ is introduced into the second (cathode) compartment of the cell followed by alkene and catalyst addition to the cell, and the cathode induces liquid phase hydroformylation when an electrical potential is applied between the anode and the cathode.

In WO 2017/014635, a method for electrochemically reducing carbon dioxide is described. The method involves the conversion of $CO_2$ into one or more platform molecules such as syngas, alkenes, alcohols (including diols), aldehydes, ketones and carboxylic acids, and also conversion of $CO_2$ into i.a. CO, hydrogen and syngas. The method does not, however, include preparation of low-module syngas for hydroformylation.

US 2014/0291162 discloses a multi-step method for preparation of various compounds, such as aldehydes, by electrolysis of previously prepared $CO_2$ and/or CO and steam. The method includes i.a. heat transfer from a heating means towards a proton-conductive electrolyser comprising a proton-conducting membrane which is arranged between the anode and the cathode.

WO 2007/109549 discloses a hydroformylation process, which comprises reacting an olefin with CO and $H_2$ over a hydroformylation catalyst in a liquid that has been volumetrically expanded with a compressed gas, such as supercritical $CO_2$.

In WO 2008/124538, a $CO_2$ negative method of preparing renewable hydrogen and trapping $CO_2$ from the air or gas streams is described. Direct current renewable electricity is provided to a water electrolysis apparatus with sufficient voltage to generate hydrogen and hydroxide ions at the cathode and protons and oxygen at the anode. These products are separated and sequestered, and the base is used to trap $CO_2$ from the air or gas streams as bicarbonate or carbonate salts. These carbonate salts, hydrogen and trapped $CO_2$ in turn can be combined in a variety of chemical and electrochemical methods to create valuable carbon-based materials made from atmospheric $CO_2$. The net effect of all processes is the generation of renewable hydrogen from water and a reduction of $CO_2$ in the atmosphere or in gas destined to enter the atmosphere.

WO 2008/124538 is very specific about the source of $CO_2$ as well as about the source of electricity used for the electrolysis as opposed to the present invention. Furthermore, in WO 2008/124538, electrolysis is only used to produce hydrogen while, in the present invention, $CO_2$ is converted to CO by high-temperature electrolysis.

Finally, US 2011/0253550 discloses a method for producing a synthetic material, where water is converted into $H_2$ and $O_2$ using high-temperature electrolysis. Depending on how the catalytic process is carried out, the mixture of water vapor, $CO_2$ and $H_2$ can additionally be converted catalytically into functionalized hydrocarbons, such as aldehydes. This publication is very unspecific and does not define the concept of high-temperature electrolysis, neither in terms of temperature range nor in terms of the kind(s) of equipment being usable for the purpose.

DETAILED DESCRIPTION

Now it has turned out that the above-described elements of risk in relation to syngas can effectively be counteracted by generating the syngas, which is necessary for hydroformylation plants, in an apparatus based on solid oxide electrolysis cells (SOECs) or SOEC stacks. A solid oxide electrolysis cell is a solid oxide fuel cell (SOFC) run in reverse mode, which uses a solid oxide electrolyte to produce e.g. oxygen and hydrogen gas by electrolysis of water. The SOEC technology is an advantageous alternative to low-temperature electrolysis technologies because of its high efficiency. The turn-on/turn-off of the apparatus is very swift, which is a further advantage.

In practice it will usually be desirable to operate the SOEC stack at less than full conversion, and therefore the product gas from the SOEC or SOEC stack will contain $H_2$ and $H_2O$.

In one embodiment of the invention, the raw product gas from the SOEC or SOEC stack is cooled, whereby most of the steam will condense, so that it can be separated from the gas stream as liquid water in a separator. The product gas may be further dried, e.g. over a drying column, if desired. The product gas, now containing $H_2$ as the main component, is then transferred to the RWGS reactor which is co-fed with $CO_2$. This embodiment has the advantage of pushing the equilibrium in the RWGS reaction in the direction of formation of CO and $H_2O$.

In another embodiment of the invention, the raw product gas from the SOEC or the SOEC stack is not cooled, but rather transferred directly to the RWGS reactor which is co-fed with $CO_2$. This embodiment has the advantage that the preferred operation temperatures of the SOEC or SOEC stack and the RWGS reactor are close lying; e.g. 700° C.

After the RWGS reactor, the syngas will contain $H_2$, CO, $H_2O$ and $CO_2$. By cooling the gas, most of the $H_2O$ can be brought to condense and thus easily be separated from the gas. Further drying of the syngas may be carried out by using e.g. a drying column.

The separation of $CO_2$ from the reactive components CO and $H_2$ is more complicated and costly than the separation of water from the product gas. It can be done by using a PSA (pressure swing adsorption) unit, but such a unit is expensive. However, the presence of $CO_2$ in the hydroformylation reaction actually is an advantage: The hydroformylation reaction is carried out in a liquid medium. Pressurizing this liquid with $CO_2$ leads to the so-called $CO_2$-expanded liquid (CXL). It has been described in the literature (see Fang et al. *Ind. Eng. Chem. Res.* 46 (2007) 8687-8692 and references therein) that CXL media alleviates mass transfer limitations in the hydroformylation reaction and increases the solubility of the reactant gases in the CXL medium compared to the neat liquid medium. As a result of this, the rate of the hydroformylation reaction may be increased by up to a factor of four in CXL-media compared to neat organic solvents. Furthermore, the n/iso ratio (the ratio between linear and branched aldehydes) may be improved by using a CXL solvent compared to using the neat solvent as taught in U.S. Pat. No. 7,365,234.

Therefore, the present invention offers a way to provide a syngas with the appropriate $H_2$/CO ratio while at the same time providing the $CO_2$ needed for obtaining a $CO_2$-expanded liquid reaction medium for the hydroformylation process.

An example of an olefin used for the hydroformylation reaction is 1-octene, but in principle any olefin may be used according to the present invention. An example of a liquid solvent for the hydroformylation reaction is acetone, but a long range of other organic solvents may be used.

So it is the intention of the present invention to provide a syngas-generating apparatus based on a combination of solid oxide electrolysis cells and an RWGS reactor, which can generate syngas for hydroformylation plants. The raw materials for generating the syngas will be $CO_2$ and $H_2O$.

A solid oxide electrolysis cell system comprises an SOEC core wherein the SOEC stack is housed together with inlets and outlets for process gases. The feed gas or "fuel gas" is led to the cathode part of the stack, from where the product gas from the electrolysis is taken out. The anode part of the stack is also called the oxygen side, because oxygen is produced on this side. In the stack, $H_2$ is produced from $H_2O$, which is led to the fuel side of the stack with an applied current, and excess oxygen is transported to the oxygen side of the stack, optionally using air, nitrogen, steam or carbon dioxide to flush the oxygen side.

More specifically, the principle of producing $H_2$ by using a solid oxide electrolysis cell system consists in leading $H_2O$ to the fuel side of an SOEC with an applied current to convert $H_2O$ to $H_2$ and transport the oxygen surplus to the oxygen side of the SOEC. Air, nitrogen, steam or carbon dioxide may be used to flush the oxygen side. Flushing the oxygen side of the SOEC has two advantages, more specifically (1) reducing the oxygen concentration and related corrosive effects and (2) providing means for feeding energy into the SOEC, operating it endothermic. The product stream from the SOEC contains a mixture of $H_2$ and $H_2O$, which—optionally after removal of water, e.g. by condensation—can be combined with $CO_2$ in the RWGS reaction.

If $H_2O$ is fed into an SOEC stack, the output will be a mixture of $H_2O$ and $H_2$. Steam will be electrochemically converted into gaseous hydrogen according to the following reaction:

$$H_2O \text{ (cathode)} \rightarrow H_2 \text{ (cathode)} + \tfrac{1}{2}O_2 \text{ (anode)} \quad (1)$$

The reverse water gas shift (RWGS) reaction takes place in the RWGS reactor which is fed with $H_2$ (and optionally $H_2O$) from the SOEC stack and $CO_2$:

$$H_2 + CO_2 \leftrightarrow H_2O + CO \quad (2)$$

When pure $H_2O$ is fed into the SOEC stack, the conversion $X_{H2O}$ of $H_2O$ to $H_2$ is given by Faraday's law of electrolysis:

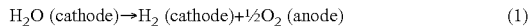
$$X_{H_2O} = \frac{p_{H_2}}{p_{H_2} + p_{H_2O}} = \frac{i \cdot V_m \cdot n_{cells}}{z \cdot f_{H_2O} \cdot F} \quad (3)$$

where $p_{H2}$ is the partial pressure of $H_2$ at cathode outlet, $p_{H2O}$ is the partial pressure of steam at cathode outlet, i is the electrolysis current, $V_m$, is the molar volume of gas at standard temperature and pressure, $n_{cells}$ is the number of cells in an SOEC stack, z is the number of electrons transferred in the electrochemical reaction, $f_{H2O}$ is the flow of gaseous steam into the stack (at standard temperature and pressure), and F is Faraday's constant.

The equilibrium constant for the RWGS reaction, $K_{RWGS}$, is given by:

$$K_{RWGS} = \frac{p_{CO} \cdot p_{H_2O}}{p_{CO_2} \cdot p_{H_2}} = \exp\left(-\frac{\Delta G}{RT}\right) \quad (4)$$

where $\Delta G$ is the Gibbs free energy of the reaction at the operating temperature, R is the universal gas constant, and T is absolute temperature.

The equilibrium constant, and therefore the extent to which electrochemically produced $H_2$ is used to convert $CO_2$ into CO, is temperature-dependent. For example, at 500° C., $K_{RWGS}$=0.195. At 600° C., $K_{RWGS}$=0.374. At 700° C., $K_{RWGS}$=0.619.

Thus, the present invention relates to a method for the generation of a gas mixture comprising carbon monoxide, carbon dioxide and hydrogen for use in hydroformylation plants, comprising the steps of:
evaporating water to steam,
feeding the steam to a solid oxide electrolysis cell (SOEC) or an SOEC stack at a sufficient temperature for the cell or cell stack to operate while supplying an electrical current to the cell or cell stack to effect a partial conversion of steam to hydrogen,
optionally removing some of or all the remaining steam from the raw product gas stream by cooling the raw product gas stream allowing for condensation of at least part of the steam as liquid water and separating the remaining product gas from the liquid,
utilizing the effluent SOEC gas comprising $H_2$ together with $CO_2$ from an external source as feed for a RWGS reactor in which the RWGS reaction takes place, converting some of the $CO_2$ and $H_2$ to CO and $H_2O$,
removing some of or all the remaining steam from the raw product gas stream by cooling the raw product gas stream allowing for condensation of at least part of the steam as liquid water and separating the remaining product gas from the liquid, and
using said gas mixture containing CO, $CO_2$ and $H_2$ for liquid phase hydroformylation utilizing carbon monoxide and hydrogen as reactants, while recycling $CO_2$ to the RWGS reactor.

Preferably the temperature, at which $H_2$ is produced by electrolysis of $H_2O$ in the SOEC or SOEC stack, is around 700° C.

One of the great advantages of the method of the present invention is that the syngas can be generated with the use of virtually any desired $CO/H_2$ ratio, since this is simply a matter of adjusting the $CO_2/H_2O$ ratio of the feed gases.

Another great advantage of the invention is, as already mentioned, that the syngas can be generated "on-site", i.e. exactly where it is intended to be used, instead of having to transport the toxic and highly flammable syngas from the preparation site to the site of use.

Yet another advantage of the present invention is that if it is desired to switch between a low module syngas and pure Hz, this can be done using the same apparatus by simply bypassing the RWGS reactor when pure hydrogen is needed.

A further advantage of the present invention is that it provides a $CO/H_2$ stream diluted in $CO_2$ which enables the subsequent hydroformylation reaction to be carried out in a $CO_2$-expanded liquid (CXL) reaction medium. These advantages embrace higher reaction rates, improved selectivity (n/iso ratio) at mild conditions (lower temperature and lower pressure) compared to hydroformylation in a neat liquid media.

A still further advantage of the present invention is that syngas of high purity can be produced without in any way being more expensive than normal syngas, even though this desired high purity would prima facie be expected to entail increased production costs. This is because the purity of the syngas is largely determined by the purity of the $CO_2/H_2O$ feed, and provided that a feed consisting of food grade or beverage grade $CO_2$ and ion-exchanged water is chosen, very pure syngas can be produced.

The invention is illustrated further in the examples which follow.

Example 1

$H_2O$ Electrolysis

An SOEC stack consisting of 75 cells is operated at an average temperature of 700° C. with pure steam fed to the cathode at a flow rate of 100 Nl/min steam (corresponding to a liquid water flow rate of approximately 80 g/min), while applying an electrolysis current of 50 A. Based on equation (3), the conversion of $H_2O$ under such conditions is 26%, i.e. the gas exiting the cathode side of the stack is 26% $H_2$, 74% $H_2O$.

Example 2

$H_2O$ Electrolysis Combined with RWGS

An SOEC stack consisting of 75 cells is being operated at an average temperature of 700° C. with steam fed to the cathode with a total flow rate of 100 Nl/min, while applying an electrolysis current of 50 A. In the stack, steam is electrochemically converted into $H_2$ according to reaction (1) at a conversion of 52%. This effluent gas is fed directly from the SOEC to the RWGS reactor together with 100 Nl/min $CO_2$. The overall $H_2O/CO_2$ feed ratio is thus 50:50. The gas feeding the RWGS reactor will have the following composition: 0% CO, 50% $CO_2$, 26% $H_2$ and 24% $H_2O$. Due to the RWGS reaction, some of the hydrogen will be used to generate CO. The RWGS reactor is operated isothermally at 700° C. Therefore, the gas exiting the RWGS reactor will have the following composition: 10.7% CO, 39.3% $CO_2$, 15.3% $H_2$ and 34.7% $H_2O$. The ratio of CO:$H_2$ in the product gas is thus 1:1.43.

Example 3

$H_2O$ Electrolysis Combined with RWGS

This example is carried out as Example 2 except that the overall $H_2O/CO_2$ feed ratio is 41:59. The gas exiting the RWGS reactor will have the following composition: 13.2% CO, 45.8% $CO_2$, 13.0% $H_2$ and 28.0% $H_2O$. The ratio of CO:$H_2$ in the product gas is thus approximately 1:1.

Example 4

$H_2O$ Electrolysis Combined with RWGS

This example is carried out as Example 2 except that the effluent cathode gas from the SOEC stack is cooled, whereby steam condenses as liquid water which is taken out in a separator. The gas feeding the RWGS reactor will therefore have the following approximate composition: 0% CO, 50% $CO_2$, 50% $H_2$ and 0% $H_2O$. Due to the RWGS reaction, some of the hydrogen will be used to generate CO. The RWGS reactor is operated isothermally at 700° C. Therefore, the gas exiting the RWGS reactor will have the following approximate composition: 22% CO, 28% $CO_2$, 28% $H_2$ and 22% $H_2O$. The ratio of CO:$H_2$ in the product gas is thus 1:1.27.

The invention claimed is:

1. A method for the generation of a gas mixture comprising carbon monoxide, carbon dioxide and hydrogen for use in hydroformylation plants, comprising the steps of:
    evaporating water to steam,
    feeding the steam to a solid oxide electrolysis cell (SOEC) or an SOEC stack at a sufficient temperature for the cell or cell stack to operate while supplying an electrical current to the SOEC or SOEC stack to effect a partial conversion of steam to hydrogen forming a raw product gas,
    feeding $CO_2$ from an external source,
    utilizing the raw product gas comprising $H_2$ together with the $CO_2$ as feed for a reverse water gas shift (RWGS) reactor in which the RWGS reaction takes place, converting some of the $CO_2$ and $H_2$ to CO and $H_2O$ forming a RWGS product gas, wherein the raw product gas is transferred directly to the RWGS reactor without cooling the raw product gas,
    removing some of or all the remaining steam from the RWGS product gas stream by cooling the RWGS product gas stream allowing for condensation of at least part of the steam as liquid water and separating a remaining product gas from the liquid water, the remaining product gas comprising CO, $CO_2$ and $H_2$, and
    using the remaining product gas for a liquid phase hydroformylation process utilizing carbon monoxide and hydrogen as reactants.

2. The method according to claim 1, wherein the temperature, at which $H_2$ is produced by electrolysis of $H_2O$ in the SOEC or SOEC stack, is around 700° C.

3. The method according to claim 1, comprising removing essentially all the remaining steam from the RWGS product gas stream by cooling the RWGS product gas stream allowing for condensation of the steam as liquid water and separating the remaining product gas from the liquid water.

4. The method according to claim 1, further comprising recycling $CO_2$ from the remaining product gas to the RWGS reactor.

5. The method according to claim 1, further comprising utilizing the $CO_2$ to form a $CO_2$-expanded liquid (CXL) reaction medium for the hydroformylation process.

\* \* \* \* \*